(12) United States Patent
Hattori et al.

(10) Patent No.: US 7,294,943 B2
(45) Date of Patent: Nov. 13, 2007

(54) ELECTRIC ROTATING MACHINE

(75) Inventors: Kenichi Hattori, Hitachi (JP);
Kazumasa Ide, Hitachiota (JP);
Akiyoshi Komura, Hitachi (JP);
Takashi Watanabe, Hitachi (JP);
Ryoichi Shiobara, Hitachi (JP);
Yasuomi Yagi, Hitachi (JP); Kengo Iwashige, Hitachi (JP); Keiji Kobashi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 83 days.

(21) Appl. No.: 11/265,227

(22) Filed: Nov. 3, 2005

(65) Prior Publication Data

US 2006/0055255 A1    Mar. 16, 2006

Related U.S. Application Data

(63) Continuation of application No. 10/469,763, filed as application No. PCT/JP02/01952 on Mar. 4, 2002, now Pat. No. 7,071,586.

(30) Foreign Application Priority Data

Mar. 7, 2001 (WO) ........................ PCT/JP01/01775
Mar. 29, 2004 (JP) ............................ 2004-096242

(51) Int. Cl.
*H02K 9/00* (2006.01)
(52) U.S. Cl. .............................. 310/58; 310/52; 310/59
(58) Field of Classification Search ............ 310/52–59, 310/60 R–61
See application file for complete search history.

(56) References Cited

U.S. PATENT DOCUMENTS 1,594,058 A    7/1926   Freiburghouse
2,695,368 A   11/1954   Kilbourne
2,742,582 A    4/1956   Bahn et al.
2,887,593 A    5/1959   Wiedemann
3,110,827 A   11/1963   Baudry
3,739,208 A    6/1973   Shartrand
4,051,400 A    9/1977   Armor et al.
4,071,790 A    1/1978   Darby et al.
4,383,191 A    5/1983   Mizuyama et al.
4,546,279 A   10/1985   Hammer et al.
4,547,688 A   10/1985   Hammer et al.
5,633,543 A    5/1997   Jarczynski et al.
5,652,469 A    7/1997   Boardman et al.
6,097,116 A    8/2000   Hess et al.
6,124,653 A    9/2000   Hediger et al.
6,201,323 B1   3/2001   Semba et al.
6,262,502 B1   7/2001   Semba et al.
6,359,350 B1   3/2002   Kaiho et al.

(Continued)

FOREIGN PATENT DOCUMENTS

DE          40 32 944 A1    6/1991

(Continued)

*Primary Examiner*—Thanh Lam
(74) *Attorney, Agent, or Firm*—McDermott Will & Emery LLP

(57) ABSTRACT

An electric rotating machine capable of lowering the temperature of a rotor disposed, wherein at least one of closed ventilation loops for cooling is formed, one of the loops constituting a ventilation passage communicating with an exhaust side through a heat source of the end of the generator to a cooler, thereby to supply cooling wind to the rotor after it passes through the cooler.

24 Claims, 9 Drawing Sheets

U.S. PATENT DOCUMENTS

| | | | |
|---|---|---|---|
| 6,891,290 B2 * | 5/2005 | Nagayama et al. | 310/58 |
| 7,141,898 B2 * | 11/2006 | Thiot | 310/55 |
| 2003/0020339 A1 * | 1/2003 | Ide et al. | 310/58 |
| 2004/0066099 A1 * | 4/2004 | Weeber et al. | 310/58 |
| 2004/0084976 A1 * | 5/2004 | Thiot | 310/58 |
| 2006/0055255 A1 * | 3/2006 | Hattori et al. | 310/58 |

FOREIGN PATENT DOCUMENTS

| | | |
|---|---|---|
| EP | 0 522 210 A1 | 1/1993 |
| EP | 1005139 A | 11/1999 |
| JP | 52009807 | 1/1977 |
| JP | 56078352 A | 6/1981 |
| JP | 57040343 A | 3/1982 |
| JP | 57-78351 A | 5/1982 |
| JP | 57078351 | 5/1982 |
| JP | 58009545 A | 1/1983 |
| JP | 58015450 | 1/1983 |
| JP | 58222755 | 12/1983 |
| JP | 59113736 | 6/1984 |
| JP | 59172953 A | 9/1984 |
| JP | 04351439 | 12/1992 |
| JP | 10-150740 | 6/1998 |
| JP | 2000-125511 A | 4/2000 |
| JP | 2000125511 | 4/2000 |
| JP | P2000-125511 A | 4/2000 |
| JP | 2000-299951 A | 10/2000 |
| JP | 2000308311 A | 11/2000 |

* cited by examiner

ELECTRIC ROTATING MACHINE

RELATED APPLICATIONS

This application is a continuation of application Ser. No. 10/469,763, filed Sep. 4, 2003, now U.S. Pat. No. 7,071,586 which is a U.S. National Phase under 35 U.S.C. 371 of International Application No. PCT/JP02/01952, filed Mar. 4, 2002, which in turn claims the benefit of Japanese Application No. 2004-096242, filed Mar. 29, 2004 claims priority of Application No. PCT/JP01/01775, filed Mar. 7, 2001, the contents of which are hereby incorporated by reference.

BACKGROUND TECHNOLOGY

An electric rotating machine is a machine for rotating a rotor located in an opposite relation with a stator. The rotor and stator are heat generation sources due to iron loss or copper loss, etc. In order to suppress the temperature elevation in the rotating machine, the machine is cooled with a coolant. Generally, gaseous coolants such as hydrogen gas or air are widely used as the coolant. When air is used as the coolant, ducts that penetrate the radial direction or the axial direction are disposed in the rotor and stator, the ducts. A fan for compressing air is disposed at the end of the rotating shaft; the rotor and the stator are cooled by causing the air to pass through the ducts.

A technology for cooling the rotor and stator is disclosed in Japanese Patent Laid-open print 10-150740, Japanese Patent Laid-open print 2000-125511. According to the technology, air streams merge in front of the fan disposed to the end of the rotor shaft, after the air passes through the ducts that penetrate the rotor and stator.

The air stream is energized by the rotation of the fan and again distributed. One of the distributed cooling air streams is guided to the stator, and the other is guided to the rotor.

In the technology disclosed in Japanese Patent Laid-open print 10-150740, the merged air streams are cooled with a relatively large cooler. After the air is cooled in the cooler, it is distributed to the stator and the rotor.

In the technology disclosed in Japanese Patent Laid-open 2000-125511, the merged air streams are distributed into two streams, and then the streams are guided to different coolers to be cooled separately. One of the air streams is guided to the stator and the end of the windings, and the other to the rotor.

DESCRIPTION OF INVENTION

In the above-mentioned prior art, a sufficient cooling was not performed. That is, since one of the distributed air streams is guided to the stator, and the other to the rotor; cooling of the rotor was not sufficient because the air is guided to the rotor after it is heated by passing through the fan.

Although a technology was known wherein the fan was disposed in the opposite direction, wherein air that has passed through the cooler is supplied to the rotor and stator, cooling air of highest temperature concentrates on the end portions of windings of the stator. At the same time, supply of cooling air to the end portions of the ventilationing was insufficient. Moreover, the structure was complicated and the machine should become large in size.

An object of the present invention is to provide a rotating machine that eliminates one or more of the above-mentioned problems.

In order to achieve the object, the present invention provides an electric rotating machine comprising a stator ventilation duct or ducts disposed in a stator, a rotor ventilation duct disposed in a rotor, an entrance port communicated with the rotor ventilation duct, and a first ventilation passage for guiding gas that has passed through the rotor ventilation duct and then passed through the stator duct to the entrance port, wherein gas to be aspirated by a fan is separated in the vicinity of the fan to prevent mixing of the gas with gas introduced into the entrance port, wherein the gas compressed by the fan is guided through the first ventilation passage to the entrance port, and wherein the gas that has passed through the rotor ventilation duct and then passed through the stator ventilation duct is guided to the first ventilation passage after the gas passes through the stator ventilation duct.

The present invention provides an electric rotating machine comprising a stator ventilation duct disposed in a stator, a rotor ventilation duct disposed in a rotor, an entrance port communicated with the rotor ventilation duct, and a first ventilation passage for guiding the gas that has passed through the stator ventilation duct after passing through the rotor ventilation duct to the entrance port, without passing through the fan, wherein the gas that has passed through the stator ventilation duct after passing through the rotor ventilation duct is guided to the first ventilation passage after it is cooled in the cooler.

The present invention provides an electric rotating machine comprising an entrance port communicated with a rotor ventilation duct, wherein gas that has passed through the rotor ventilation duct is guided to a stator ventilation duct, the gas having passed through the stator ventilation duct is guided to a first cooler, the gas having passed through the fist cooler is guided to a second cooler, and the gas having passed through the second cooler is guided to the entrance port, without passing through a fan.

The present invention provides another electric rotating machine comprising a stator ventilation duct disposed in a stator, a rotor ventilation duct disposed in a rotor, an entrance port communicated with the rotor ventilation duct, and a first ventilation passage for guiding gas that has passed through the rotor ventilation duct and the stator ventilation duct to the entrance port, wherein gas to be aspirated by a fan is separated in the vicinity of the fan to prevent mixing of the gas with gas introduced into the entrance port, wherein the gas compressed by the fan is guided through the first ventilation duct to the entrance port, and wherein the gas that has passed through the rotor ventilation duct and the stator ventilation duct is guided to the first ventilation passage after the gas is cooled with a cooler.

The present invention further provides an electric rotating machine comprising a stator ventilation duct disposed in a stator, a rotor ventilation duct disposed in a rotor, and a first ventilation passage for guiding gas that has passed through at least one of the rotor ventilation duct and the stator ventilation duct to an entrance port, wherein gas to be aspirated by a fan is separated in the vicinity of the fan to prevent mixing of the gas with gas introduced into the entrance port, wherein the gas compressed by the fan is guided through the first ventilation passage to the entrance port, and wherein the gas that has passed through the rotor ventilation duct and the stator ventilation passage is guided to the first ventilation duct after the gas passes through the stator ventilation duct.

The present invention also provides an electric rotating machine comprising a stator ventilation duct disposed in a stator duct, a rotor ventilation duct disposed in a rotor, a first ventilation passage for guiding gas that has passed through the stator ventilation duct and gas that has passed through the rotor ventilation duct, an entrance port communicated with the rotor ventilation duct, and a cooler disposed on a ventilation passage communicated between an exhaust side of the fan and the entrance port, wherein gas aspirated into a fan is separated in the vicinity of the fan to prevent mixing of the gas and the gas introduced into the entrance port near the fan, and wherein the gas compressed by the fan is introduced into the entrance port and the gas that has passed through the rotor ventilation duct passes through the stator ventilation duct.

The present invention provides an electric rotating machine having a rotor ventilation duct, wherein gas biased by a fan passes through an end of a stator, and the gas that has passed through the end of the stator passes through a cooler, and wherein the gas aspirated into the fan is separated from mixing of the gas with gas introduced into the entrance port, and the gas is introduced into the entrance port side.

The present invention provides an electric rotating machine having a stator ventilation duct disposed in a stator, a rotor ventilation duct disposed in a rotor and a ventilation passage that rotates together with a shaft, the passage being disposed inside of the radial direction of the fan, the passage being communicated with the rotor ventilation duct, and wherein the gas compressed by the fan is guided to the passage after it is cooled with the cooler.

The present invention also provides an electric rotating machine having a stator ventilation duct disposed in a stator, a rotor ventilation duct disposed in a rotor, and a ventilation passage disposed in the inner side of the radial direction of a fan, a ventilation passage rotating together with a rotating shaft, wherein a pressure difference between a pressure of the downstream of the fan and a pressure of the ventilation passage is no less than 2 kPa.

In order to solve the above-mentioned problem, the present invention provides an electric rotating machine comprising a stator ventilation duct disposed in a stator, a rotor ventilation duct disposed in a rotor, an entrance port communicated with the rotor ventilation duct, and a first ventilation passage for guiding the gas that has passed through the stator ventilation duct after passing through the rotor ventilation duct to the entrance port, without passing through the fan, wherein the gas that has passed through the stator ventilation duct after passing through the rotor ventilation duct is guided to the first ventilation passage after it is cooled in the cooler.

The electric rotating machine of the present invention comprises an entrance port communicated with a rotating ventilation duct, wherein gas that has passed through a rotor ventilation duct is guided to the stator ventilation duct; gas that has passed through the stator ventilation duct is guided to a first cooler; and air that has passed through the first cooler is guided to a second cooler, the gas that has passed through the second cooler being guided to the entrance port without passing through a fan.

The electric rotating machine of the present invention comprises a first ventilation passage for guiding gas that has passed through a stator ventilation duct, together with gas that has passed through a rotor ventilation duct, an entrance port communicated with a rotor ventilation duct, and a cooler disposed in a passage communicating an exit side of a fan to the entrance port side, wherein gas that has passed through the first ventilation passage is guided to the entrance port without passing through the fan, and gas that has passed through the rotor ventilation duct is guided to the stator ventilation duct.

The present invention provides an electric rotating machine wherein gas compressed by a fan is guided to pass through the end of a stator, then pass through a cooler, thereafter is guided to a rotor ventilation duct, without passing through the fan.

The present invention provides an electric rotating machine comprising a first ventilation passage for guiding the gas that has passed through the end of a stator to a first cooler, a second ventilation passage for guiding the gas that has been cooled by the first cooler to the rotor ventilation duct, a third ventilation duct for guiding the gas that has passed through the rotor ventilation duct to the stator ventilation duct, a fourth ventilation duct for guiding the gas that has passed through the stator ventilation duct to the second cooler, and a fourth ventilation duct for guiding the gas that has passed trough the second cooler to the rotor ventilation duct, again.

The present invention provides the electric rotating machine comprising a first ventilation passage for guiding gas that has passed through the end of a stator to a first cooler, and a second ventilation passage for guiding the gas that has passed through the first cooler to the stator ventilation duct, wherein the second ventilation duct guides the gas along the outer periphery of the first cooler to the rotor ventilation duct.

The present invention further provides an electric rotating machine comprising a first ventilation passage for guiding the gas that has passed through the end of the stator to a first cooler, a second ventilation passage for guiding gas that has passed through the stator ventilation duct to a second cooler, and a third ventilation passage for guiding the gas that has passed through the first cooler to the rotor ventilation duct without passing through the fan, wherein the first ventilation passage and the second ventilation passage intersects each other.

THE BEST EMBODIMENTS FOR PRACTICING THE INVENTION

In the following, the present invention will be explained by reference to FIG. 1 that shows the whole structure of the turbine generator of the first embodiment according to the present invention.

Figure 1:
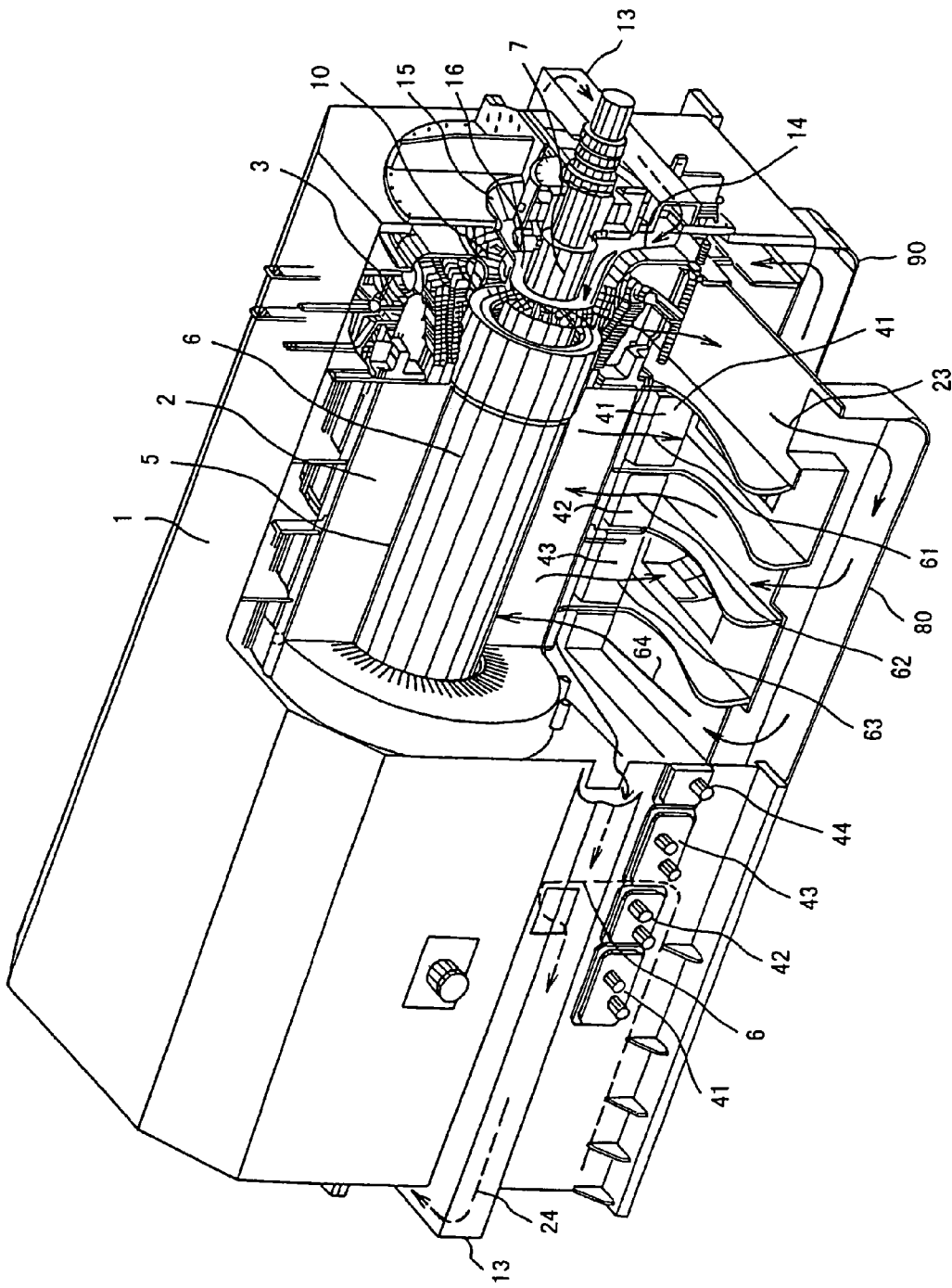
FIG. 1 shows a perspective view of a turbine generator according to the present invention.

FIG. 1 shows the whole structure of the turbine generator. As shown in FIG. 1, the generator comprises a stator core 2 and a rotor core 6 in a stator housing 1, wherein the stator core 2 has ventilation passage sections separated from each other in the axial direction. There are ventilation passages 61, 63 that guide the gas from the inner periphery to the outer periphery, and ventilation passages 62, 64 that guide the gas from the outer periphery to the inner periphery. Coolers 41, 42 for cooling a cooling medium are disposed on the outer periphery of the stator core 2.

The ventilation duct 13 disposed outside of the stator housing 1 constitutes a ventilation passage connecting the exit ports of the coolers 41, 42 through the rotor. Cooling gas preferably air is supplied to the end of the passage. The end of the ventilation passage 14 is static, and the gaps between the rotating shaft 7, the fan 10 and the fan-ring 15 for fastening the fan have a sealing structure for preventing leakage of wind.

Further, the stator housing has the ventilation duct 80 for guiding the cooling medium exhausted from the fan 10 to the coolers 42, 44, and there is a ventilation duct 90 by which cooling wind exhausted from the coolers 41, 43 is guided to the fan 10.

The ventilation duct 80 guides the cooling medium, which was cooled with the cooler, to the rotor without passing through a heat source such as the fan. The cooling medium in the ventilation duct 80 has been compressed by the fan and has the same pressure as that of the exit of the rotor, that is, the air gap between the rotor core 6 and the stator core 2; as a result, the cooling medium flows out from the entrance port of the rotor to exit of the rotor by the action of the centrifugal force due to the rotation of the rotor core 6 thereby cooling the every part of the rotor.

Since the cooling medium impinging the rotor does not pass through the heat source such as the fan after it has passed through the coolers 42, 44, it keeps low temperature until it arrives at the entrance port of the rotor.

On the other hand, the ventilation duct 90 guides the cooling medium to the fan to compress it, after the coolers cool it. In this structure, the cooling medium that has passed through the fans to have a turbulent flow impinges the end of the stator without receiving affect of the temperature increase by a heat source other than the fan, and hence it cools the end portion effectively.

Figure 2:
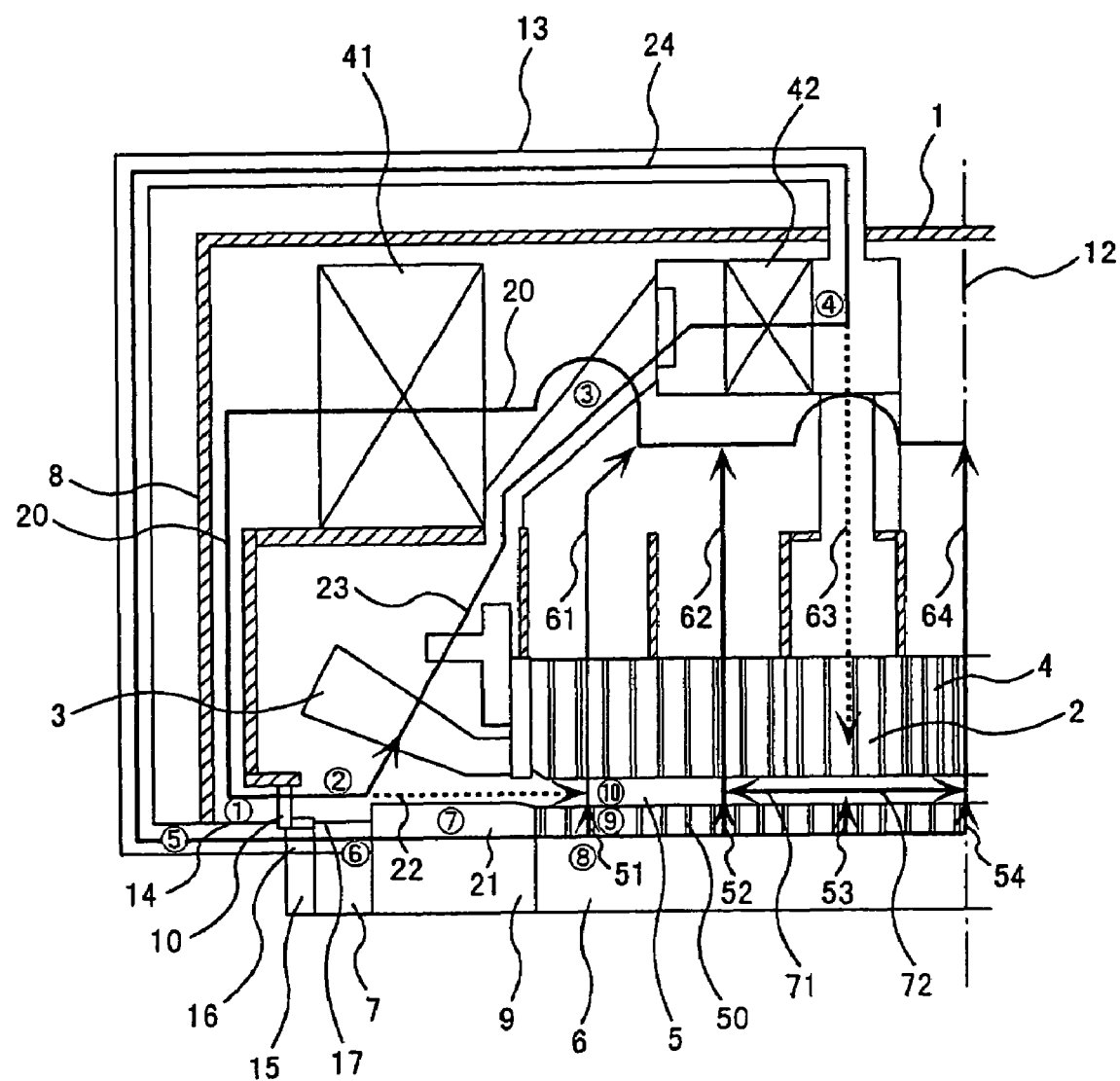
FIG. 2 is a diagrammatic view of a turbine generator according to the first embodiment of the present invention.

FIG. 2 shows a ventilation structure of the turbine generator according to one embodiment of the present invention. As shown in FIG. 2, the structure has the stator housing 1 and the stator core 2 therein. The stator core 2 has a cylindrical shape, and the stator core has slots for receiving stator windings 3. The slots are formed in the axial direction of the core in the inner periphery thereof.

The rotor core 6 is disposed around the inner periphery of the stator core 2 with the air gap 5. The rotor core 6 has the rotating shaft 7 that is united with the rotor core 6. The rotating shaft 7 extends from the center of the both ends of the rotor core 6 in the axial direction of the shaft. The rotating shaft is supported by bearings disposed in the inner periphery of the end-bracket for closing the both ends of the stator housing 1.

A plurality of slots extending in the axial direction of the rotating shaft is formed in the outer periphery of the rotor core, thereby receiving rotor windings. The retaining ring 9 fixes the both ends of the rotor windings. The rotor core 6 has a plurality of ventilation ducts 50 that are continuous around the radial direction and divided into several sections arranged in the axial direction. The end of the rotating shaft has the fan 10. The retaining ring 15 fixes the fan 10. There are ventilation passages 16, 21 that run from the fan ring 15 through the lower part of the retaining ring 9 to the rotor core 6.

The axial end of the retaining ring 9 has a cover 17 that prevents the cooling medium in the ventilation passage 22 from interference with the cooling medium in the ventilation passage 21 outside of the rotor. The ventilation structure is symmetric with respect to the central axial line 12.

The fan 10 rotates together with the rotating shaft 7, thereby circulating the cooling medium such as hydrogen gas or air filled in the machine. The machine has ventilation passages 20, 22, 23 therein, and the coolers 41, 42 for cooling the cooling medium are disposed in the middle of the passages.

The stator core 2 is divided into several sections in the axial direction; accordingly, there are ventilation passages 61, 62, 64 that ventilate from the inner diameter to the outer diameter, and ventilation passages 63 that ventilate from the outer diameter to the inner diameter. The ventilation duct 13 disposed in the outside of the stator housing 1 constitutes ventilation passage connecting from the exit of the cooler 42 to the rotor, thereby introducing the cooling medium into the rotor from the end thereof. Since the end of the ventilation duct 14 is static, and the gaps between the duct 14 and the rotating shaft 7, the fan 10, fan ring 15, etc constitute the sealing structures for preventing the leakage of the wind.

Figure 8:
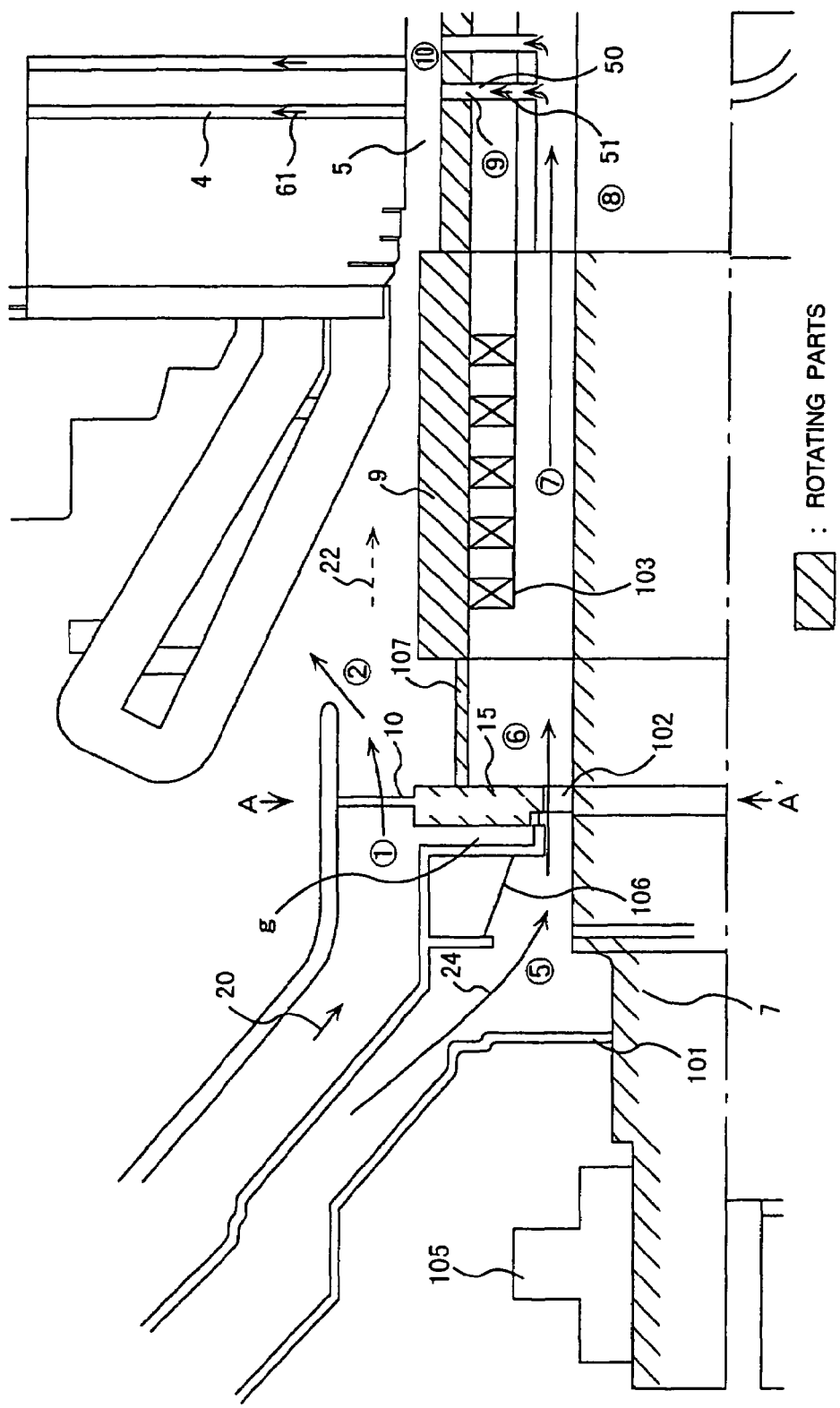
FIG. 8 shows ventilation passages in the vicinity of the rotor.

FIG. 8 shows details of the entrance port of the rotor 7. The numeral ① to ⑩ are locations indicating pressures. Details will be explained later. The cooling medium that leaves the cooler 42 arrives at the rotor through the ventilation passage 24. The hatched part in FIG. 8 is the structure of the rotor, which is constituted by the fan 10, the fan ring 15, the cover 107, the retaining ring 9 and the rotor coils, and rotates together with the rotor. On the other hand, the fan side air-seal 106 and the shaft end air seal 101 Are substructures for the stator 2.

A sealing structure is constituted, around the entrance ⑤ of the rotor, by the fan side air-seal 106 and the axial end air-seal 101, thereby maintaining the gap between the fan ring 15 and the rotor 7. Since the rotor 7 moves in the axial direction, the seal structure allows such the movement of the rotor.

Figure 9:
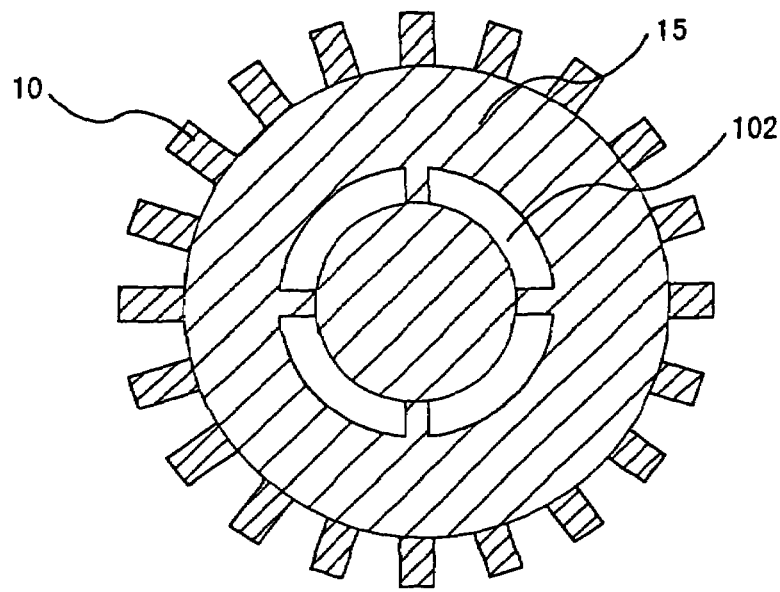
FIG. 9 is a detailed structure of the fan.

The fan ring 15 holds the fan 10 and has a ventilation passage 102. Details of the fan ring 15 is shown in FIG. 9 as a sectional view along A-A' line. Fans 10 are formed, with equal pitches, coaxially on the outer periphery of the fan ring 15. The ventilation passages 102 are formed, with equal pitches, coaxially on the inner periphery.

The cooling medium that has passed through the ventilation passage 102 formed in the fan ring 15 arrives at the inside ⑥ of the rotor 7 as shown in FIG. 8. The cover 107 separates the ventilation passage at the rotor side from the ventilation passage at the stator side. The structure cover 107 is supported by connecting with the fan ring 15 and the retaining ring 9 or fixed with a small gap. The cold wind that has passed through the section ⑥ travels below the rotor coils 103 and travels towards the axial center through sections ⑦, ⑧. The rotor 7 is supported by the bearing 105 and rotated (though the bearing is present on the other side, it is not shown).

The ventilation route till the rotor in this embodiment will be explained in detail. The ventilation passage is constituted as follows. The ventilation passage is constituted by the ventilation passage 20 from the exit of the cooler 41 to the fan 10 (a pressure ① in front of the fan), the ventilation passage 23 (a pressure ③) that runs from the fan 10 (a pressure ② at the exhaust gas) through the axial end of the stator coils 3 to the second cooler 42, the ventilation passage 24 from the exit of the second cooler 42 (a pressure ④ at the exit of the second cooler) to the entrance of the rotor, the ventilation passage 16 passing through the fan ring 15 (a pressure ⑤ in front of the fan ring 15, and a pressure ⑥ after the fan), the ventilation passage 21 passing below the cover 17 and the retaining ring 9 to the rotor core 6, the ventilation passages 51, 61 (a pressure ⑦ in front of the ventilation passage 51, and a pressure ⑧ in the ventilation passage), and the ventilation passage 20 at the outer diameter side of the stator (a pressure ⑨ in the ventilation duct 4, and a pressure ⑩ at the air gap 5). The cooling medium finally arrives at the first cooler 41.

Though the ventilation passages 51, 61 were explained as ones running in the radial direction, there are other ventilation passages 52, 62, 54, 64, etc through which the cooling medium passes, or the cooling medium passes through the ventilation passage 53, the air gap 5, ventilation passages 71, 72, etc, ventilation passages 62, 64 to the passage 20 at the outer diameter of the stator.

There are loops wherein the cooling medium passes through only the stator, without passing through the rotor. That is, the ventilation passage 22 that guides towards the air gap 5 after passing through the fan 10, and the ventilation passages 63, etc that flows towards the air gap 5 from the exit of the second cooler 42 to the stator core. The cooling medium gets together the cooling medium exhausted from the ventilation passages 51, 52, 53, 54, etc, and goes through the ventilation passages 61, 62, 64, etc and arrives at the ventilation passage 20 formed at the outer periphery of the stator.

Now, the relationship between the flow of the cooling medium and the pressure will be explained. Since the flow in the whole interior of the rotating machine is roughly determined by a flow resistance at the stator side, the rotor 6 is exposed to a certain pressure distribution. Since the ventilation duct 4 of the stator 2 is a flow resistance, the cooling medium loses pressure when it passes through the ventilation duct 4. That is, a pressure at a position (0) is almost zero (0.01 pu: the pressure difference generated by the fan is set to be 1.0 pu).

The cooling medium loses pressure as it passes through the cooler 41, and the pressure becomes nearly zero pu in the vicinity of the position ①. Although the pressure ① of the cooling medium that has passed through the cooler 42, it is compressed by the fan 10 to become the highest pressure ② (1.0 pu) cooling medium in the stator side. This wind enters the air gap 5 between the stator 2 and the rotor 7 ⑩. Although the pressure ⑩ becomes lower than the pressure at the position ②, the pressure ⑩ becomes close to that of ②, because the pressure drop between the positions ② and ⑩ is not large.

On the other hand, to the point of the rotor side, it is necessary to increase the pressure at the stator side so as to give a sufficient volume of cooling medium, because the position ⑩ is the exhaust side.

Figure 10:
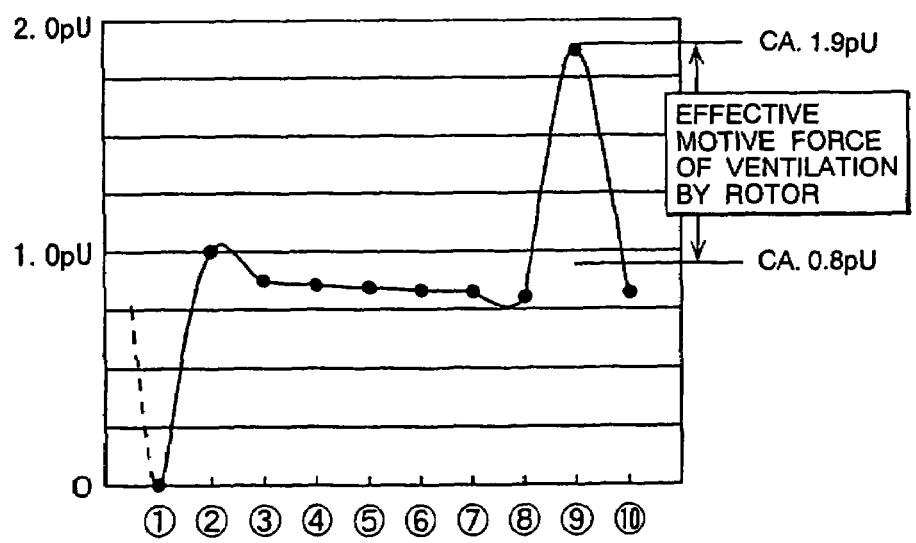
FIG. 10 is a graph showing a pressure change along the ventilation passages.

The pressure distribution observed from the rotor 7 side is shown in FIG. 10. The cooling medium compressed by the fan 10 passes through the cooler 42, and arrives at the position ④. Then, the cooling medium passing through the ventilation passage 24 by way of the position ⑤ flows through the fan ring 15 below the fan 10 to the inside ⑥ of the rotor and the position ⑦. The cooling medium loses pressure by roughly 0.01 pu at every position as it passes through the positions ④, ⑤, ⑥ and ⑦. The cooling medium at position ⑧ has a pressure of about 0.8 pu. The cooling medium that has arrived at the interior ⑧ of the rotor 7 is again compressed by the action of centrifugal force of the interior of the rotor 7 to 1.9 pu. The pressure at the position ⑨ is a motive force of cooling wind that for flowing through the rotor, and the pressure at the exit ⑩ finally becomes 0.8 pu. The volume of the cooling wind is determined by the pressure difference from this pressure.

Since the pressure at positions ① and ② is around 1.0 pu, the cooling device in an amount in accordance with the pressure difference is supplied as a driving force. As shown in FIG. 10, a large amount of the cooling medium that flows in the rotor 7 can be supplied, because the pressure difference between the positions ⑨ and ⑩, 2 kPa or more is preferable for the pressure difference of the positions ⑨ and ⑩, and 4 kPa or more is preferable, and 6 kPa or more is a further preferable pressure difference.

The relationship among the heat source, coolers and ventilation passages is as follows. The cooling wind passes through the ventilation passages 20, 23, 24, 16 and 21, where there are heat sources such as the fan 10, the end of the stator windings 3 that generates heat by copper loss. That is, the ventilation passages have an alternate arrangement of the heat sources and the coolers, such as the first cooler 41, the heat source, and the second cooler 42.

The relationship between the flow of the cooling medium and the temperature rise will be explained. The cooling medium of low temperature elevates its temperature when it passes through the fan 10, and flows into the ventilation passages 22 and 23. The cooling medium, which has entered the ventilation passage, cools the end of the stator windings to further elevate its temperature, and it flows towards the second cooler 42.

The cooling medium that has passed through the second cooler lowers its temperature and flows into the ventilation passage 63 and 24. The cooling medium towards the ventilation passage 24 passes through the ventilation passages 16, 21, 51, 52, 53, 54, etc to cool down the rotor and it elevates its temperature. Thereafter, the cooling medium of higher temperature, which is exhausted from the ventilation passage 51, merges with the cooling medium of lower temperature at the air gap 5, thereby flowing in the ventilation passages 61, 62, etc to conduct heat-exchange with the stator core 2. The cooling medium that has heat-exchanged with the stator core 2 and elevates its temperature to return to the first cooler by way of the ventilation passage.

The cooling medium of high temperature exhausted from the rotating ventilation passage 53 merges with the cooling medium exhausted from the ventilation passage 63 at around the center of the shaft, and it flows through the ventilation passages 71, 72, etc in the axial direction to merge with the cooling medium of higher temperature exhausted from the ventilation passages 52, 54.

The cooling medium exhausted from the ventilation passage 63 heat-exchanges with the stator core 2 to elevate its temperature, but its temperature is lower than the temperature of the cooling medium exhausted from the rotor ventilation passages 52, 53, 53, etc, so that the temperature of the merged cooling medium exhausted from the rotor is lower than that of the cooling medium before merging. The cooling medium passes through the ventilation passages 62, 64 to heat-exchange with the stator core 2 and elevates its temperature, followed by flowing towards the cooler 41.

According to the first embodiment having been described, the cooling medium is passed through the heat source such as the ends of the stator coils 3 from the exhaust side of the fan 10, and then it is passed through the second cooler to lower its temperature; thereafter, the cooling medium for the rotor being introduced. In this structure, since the temperature of the cooling medium can be made low, the temperature of the cooling medium after passing through the rotor can be lowered. Since the cooling medium exhausted from the rotor always passes through the ventilation duct 4, the temperature of the stator can be lowered.

Figure 3:
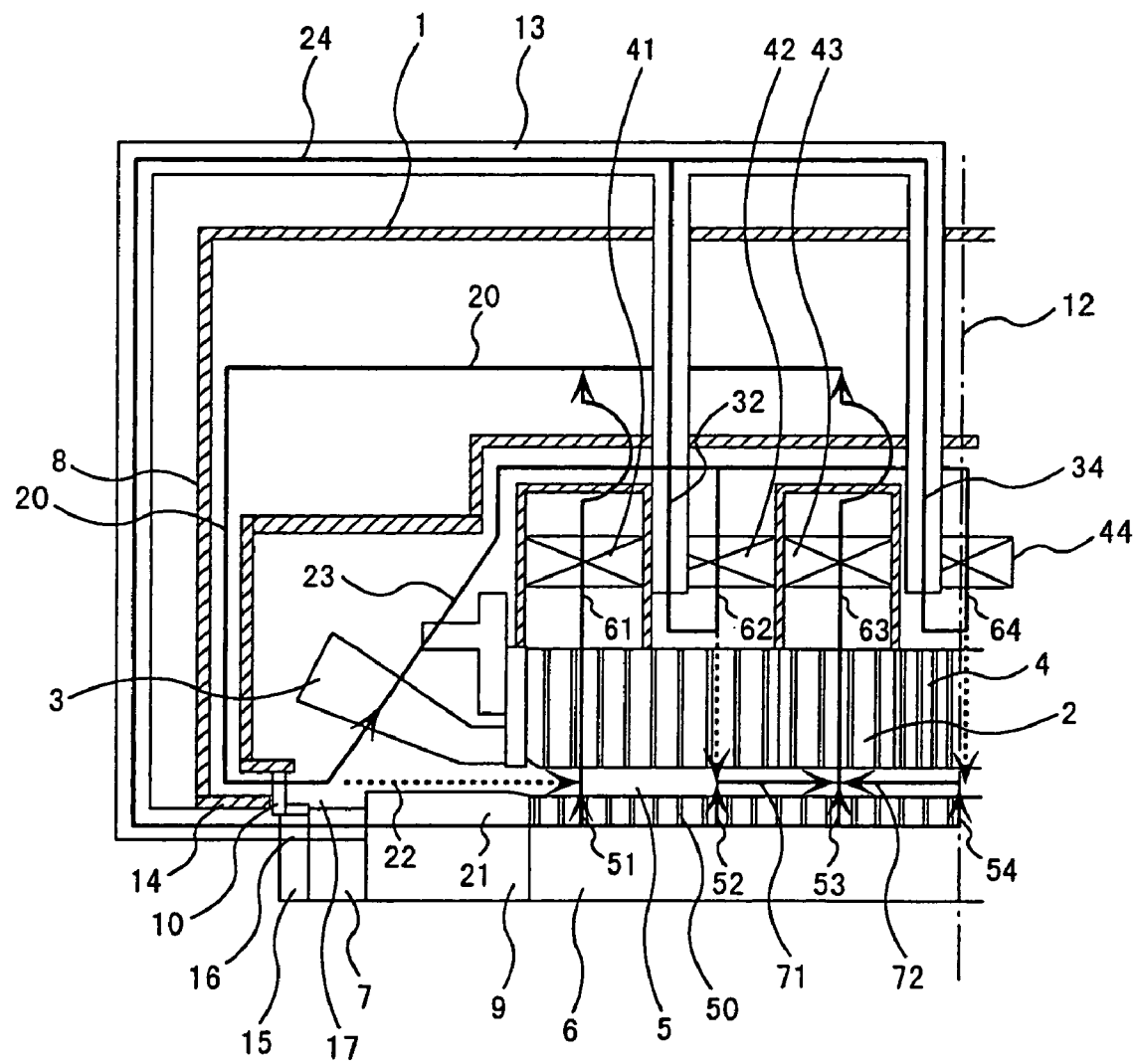
FIG. 3 is a diagrammatic view of a turbine generator according to the second embodiment of the present invention.

FIG. 3 shows the second embodiment, wherein two or more of ventilation sections that are partitioned in the axial direction of the stator core and coolers 41, 42, 43, 44, etc at the outer periphery side of the stator core 2 are disposed so that an electric rotating machine has a section where the cooling medium passes through the coolers 41, 43 after it is exhausted from the inner periphery of the stator housing 1 and a section where the cooling medium flows into the inner periphery of the stator core 2 from the inner periphery of the stator housing 1 after it passes through the coolers 42, 44.

The second embodiment is an example of application to an electric rotating machine having the ventilation passages 62, 64, etc. The cooling medium passes through the heat sources at the end of the shaft such as the fan 10, the stator coils 3, etc, and then passes through plural ventilation passages such as coolers 42, 44. The cooling medium is distributed into plural passages from the outer diameter side to the inner diameter side.

In this case, the ventilation passages 32, 34, etc are disposed in the same number as that of the ventilation sections that are directed towards the inner periphery from the outer periphery. The ventilation passages are disposed to the ventilation sections 62, 64, etc that are directed towards the inner periphery from the outer periphery. The parallel introduction of the cooling medium from the plural cooling passages can distribute load on the coolers.

Figure 4:
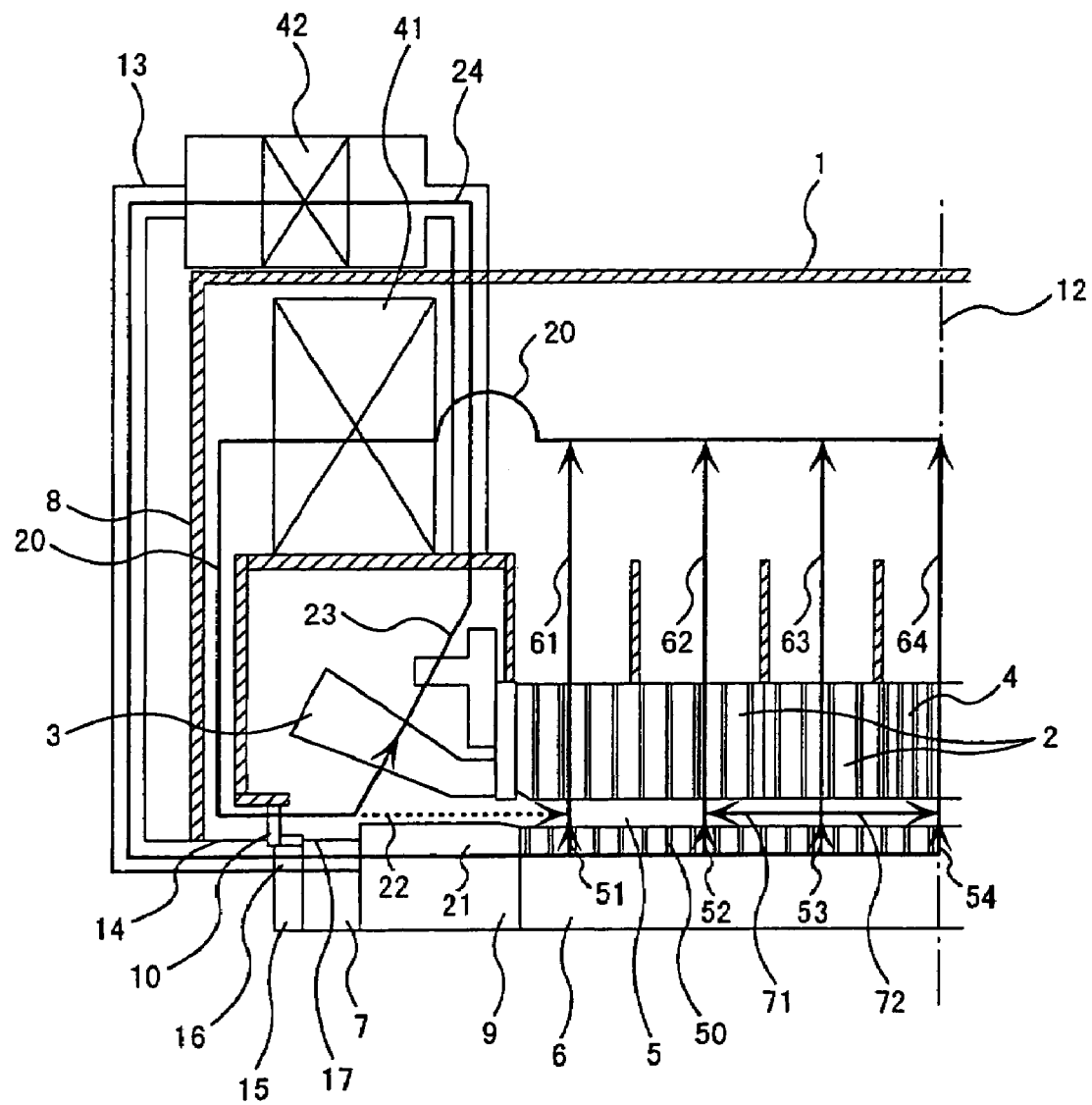
FIG. 4 is a diagrammatic view of a turbine generator according to the third embodiment of the present invention.

FIG. 4 shows a ventilation-cooling structure of the turbine generator of the third embodiment according to the present invention. The structure has the second cooler 42 disposed outside of the stator housing 1. This structure can be applied to an electric rotating machine, which ha no second cooler in the ventilation passage passing through the fan 10 and the end of the stator coils 3.

Figure 5:
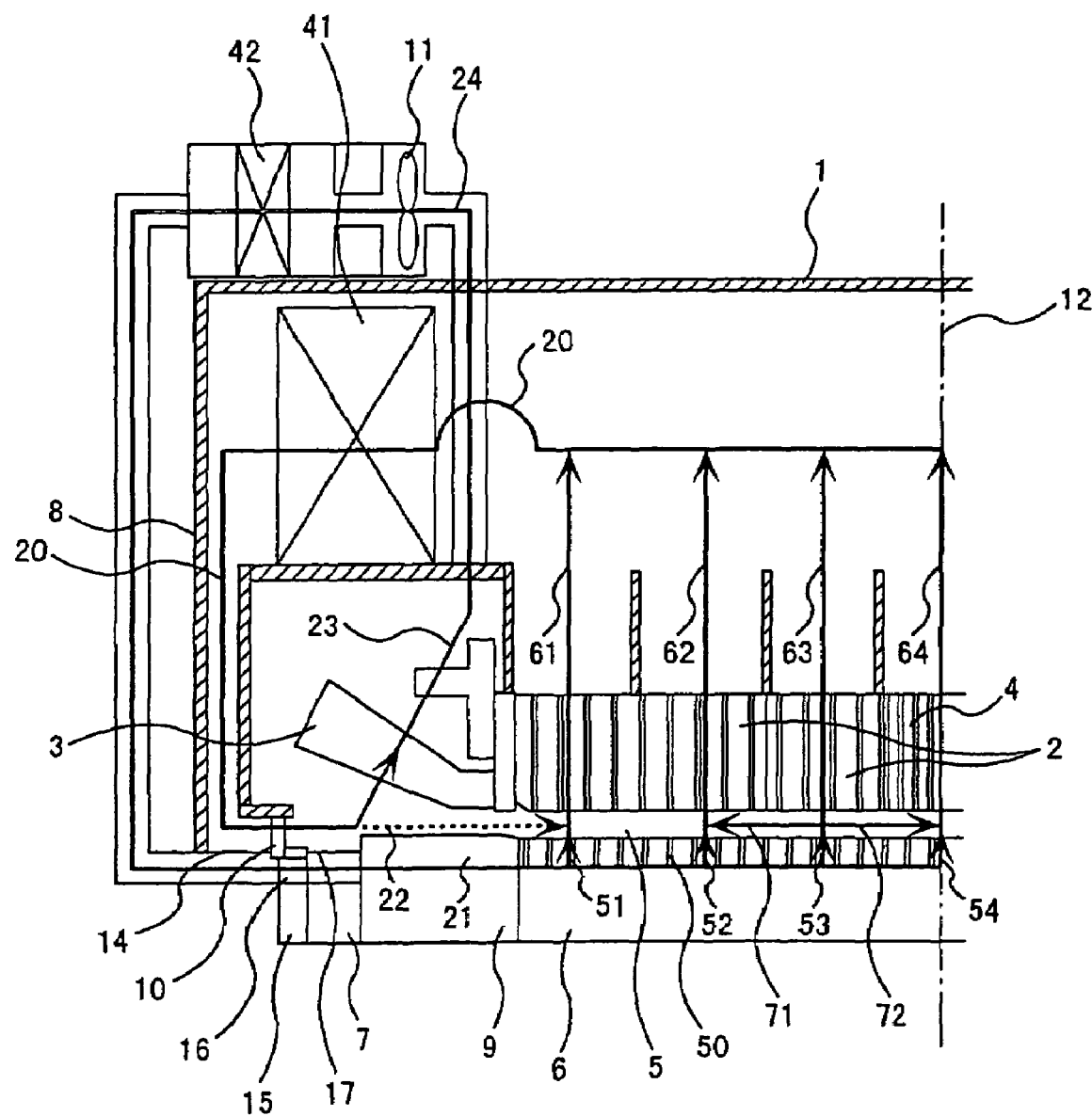
FIG. 5 is a diagrammatic view of a turbine generator according to the fourth embodiment of the present invention.

FIG. 5 shows the fourth embodiment of the structure, which has an apparatus 11 for pressurizing the cooling medium on the ventilation passage 24 that is directed to the rotor. This embodiment is useful for increasing the volume of the cooling medium in the ventilation passages 24, 21 directed to the rotor. The pressurizing apparatus 11 is disposed to the ventilation passage 23 side in front of the second cooler 42 in this case, but it can be disposed to the ventilation passage 21 side closer to the rotor than the fan 10.

Figure 6:
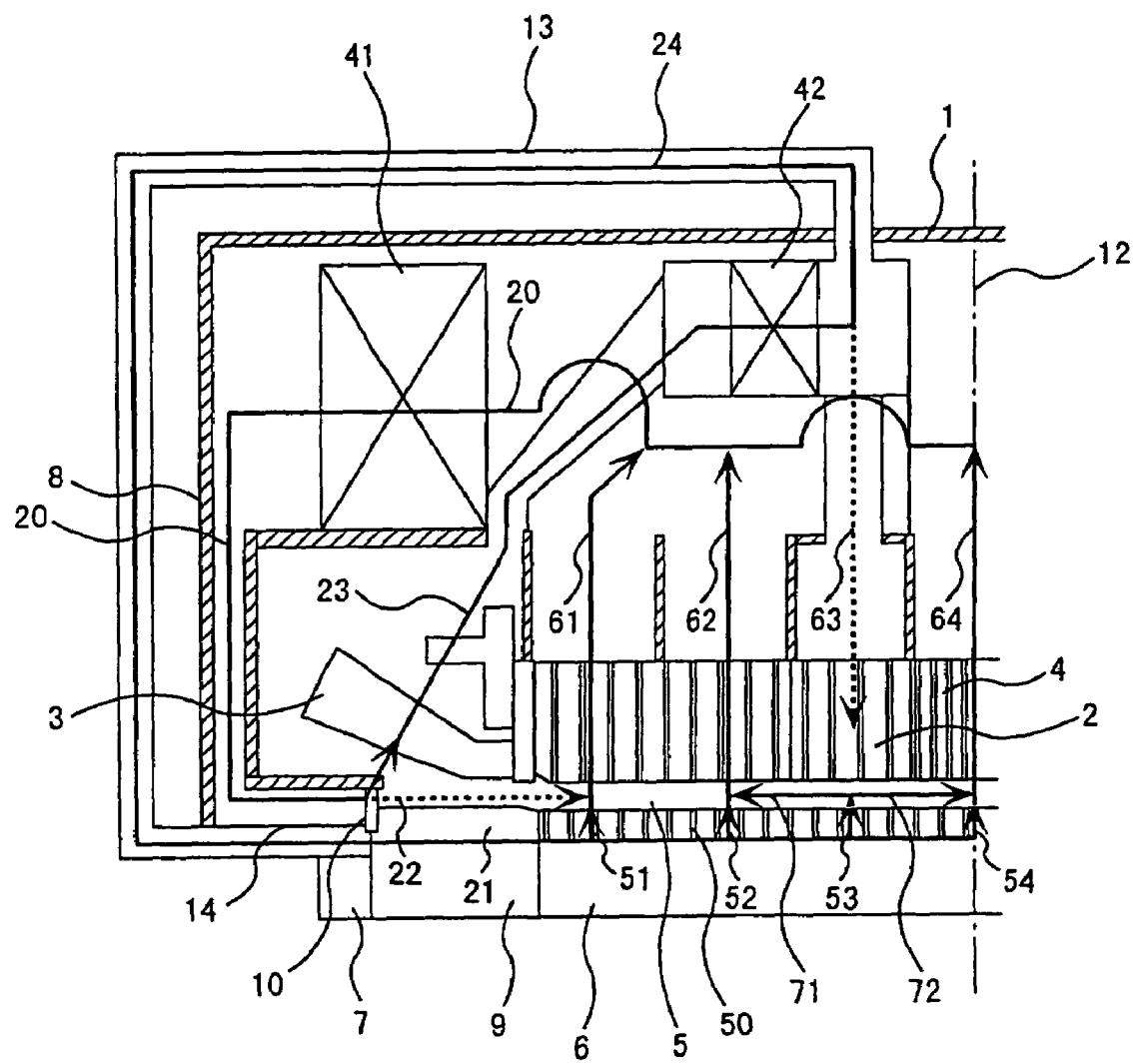
FIG. 6 is a diagrammatic view of a turbine generator according to the fifth embodiment of the present invention.

FIG. 6 shows the fifth embodiment wherein the fan 10 is disposed at the end of the retaining ring 9. In this case, the structure allows installation of another object such as a ring for fixing the fan 10 between the retaining ring 9 and the fan 10. Since this structure allows omitting the above-mentioned fan ring, it is possible to reduce ventilation resistance caused by the fan ring.

Figure 7:
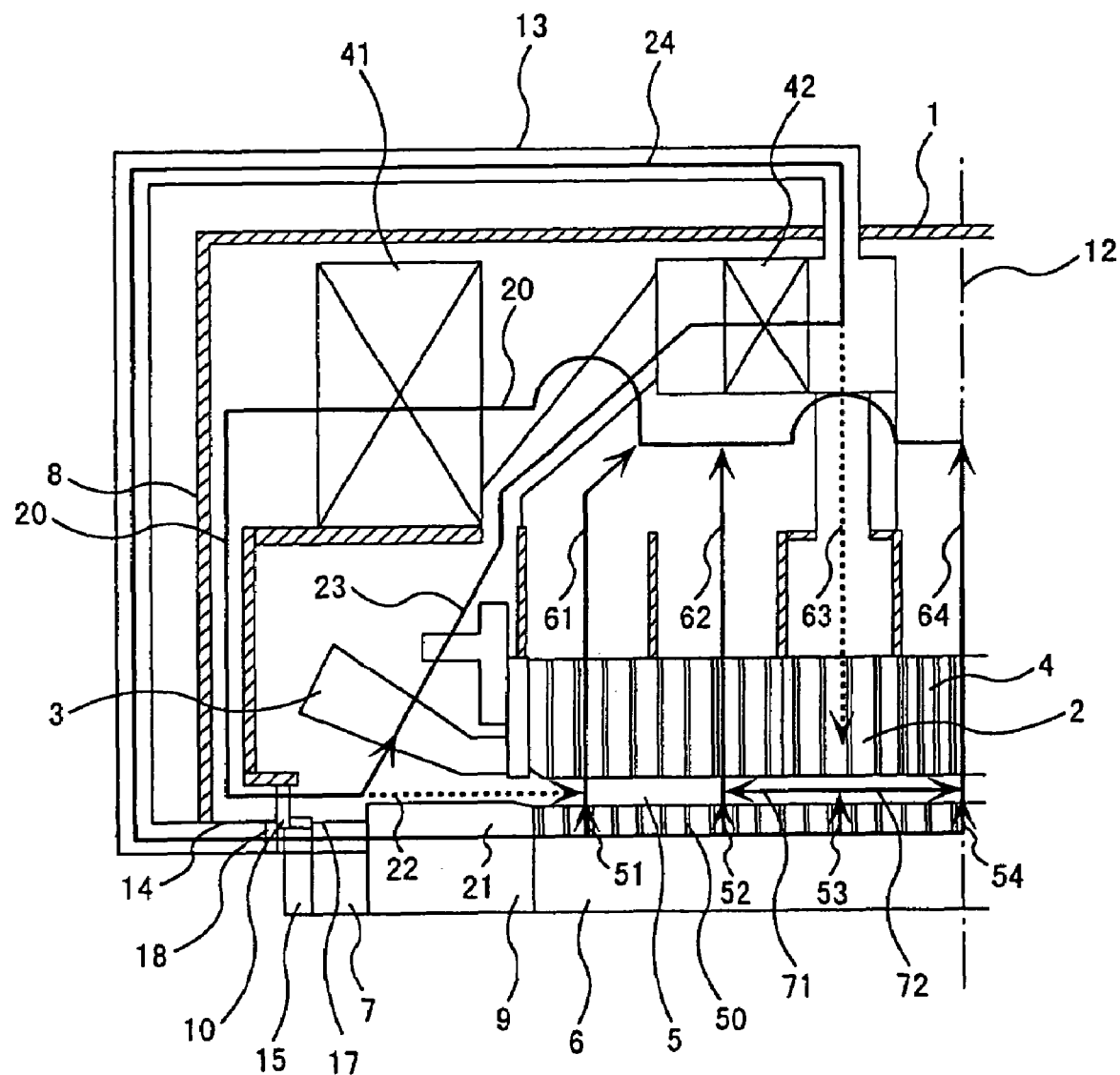
FIG. 7 is a diagrammatic view of a turbine generator according to the sixth embodiment of the present invention.

FIG. 7 shows a ventilation-cooling structure of the turbine electric generator of the fourth embodiment of the present invention, wherein a ventilation improving apparatus 18 is disposed in the ventilation passage 13 at a position near the rotor. The ventilation improving apparatus 18 increases the pressure of the cooling medium. This structure may be a structure such as a whirl structure for imparting whirl motion to the cooling medium that has passed through the ventilation passage 24, thereby to reduce ventilation resistance of the cooling medium directed to the ventilation passages 16, 21. Further, the fan ring 15 may have a function of a compressing mechanism or a structure for generating a whirl motion.

INDUSTRIAL APPLICABILITY

According to the present invention, a temperature rise of the electric rotating machine is avoided. It is possible to cool the rotor effectively by increasing the volume of the cooling gas. It is also possible to reduce a temperature rise of the rotor without local temperature rise of the rotor and stator, because the temperature of the cooling medium introduced into the rotor can be lowered without changing the ventilation passage of the cooling medium that is exhausted from the rotor.

The invention claimed is:

1. An electric rotating machine comprising a stator, a rotor rotating in opposite relation with the stator, a rotating shaft rotating with the rotor, a fan disposed in the vicinity of the end portion of the rotating shaft, a first cooler, a second cooler disposed on the axial line extending in the first cooler to the rotating shaft, a rotor ventilation duct disposed in the rotor, a stator ventilation duct disposed in the stator, and an entrance port communicated with the rotor ventilation duct, wherein gas that has passed through the rotor ventilation duct is guided to the stator ventilation duct; the gas that has passed through the stator ventilation duct is guided to the first cooler; the air that has passed through the first cooler is guided to the second cooler by way of the end portion of the stator; and part of the air that has passed through the second cooler is guided to the entrance port of the rotor ventilation duct, without passing through the fan.

2. An electric rotating machine comprising a stator, a rotor rotating in opposite relation with the stator, a rotating shaft rotating with the rotor, a fan disposed in the vicinity of the end portion of the rotating shaft, first and second coolers, a rotor ventilation duct disposed in the rotor, a stator ventilation duct disposed in the stator, and an entrance port communicated with the rotor ventilation duct, wherein gas compressed by the fan passes through the end portion of the stator; the gas that has passed through the end portion of the stator is guided to the second cooler; the gas that has passed through the second cooler is guided to the rotor ventilation duct, without passing through the fan; the gas that has passed through the rotor ventilation duct is guided to the stator ventilation duct: the gas that has passed through the stator ventilation duct is guided to the first cooler; and the air that has passed through the first cooler is guided to the fan.

3. An electric rotating machine having a first cooler and a second cooler, which comprises a stator, a rotor rotating in opposite relation with the stator, a rotor ventilation duct disposed in the rotor, a stator ventilation duct disposed in the stator, a second ventilation passage for guiding gas that has passed through end portion of the stator to the stator ventilation duct, and the second ventilation passage for guiding gas that has passed through the second cooler to the rotor ventilation duct, wherein the second ventilation passage guides gas to the rotor ventilation duct by way of the outside of the second cooler in the peripheral direction.

4. An electric rotating machine having a first cooler and a second cooler, which comprises a stator, a rotor rotating in opposite relation with the stator, a rotating shaft rotating with the rotor, a fan disposed on the rotating shaft, a stator ventilation duct disposed in the stator, and a rotor ventilation duct disposed in the rotor, which further comprises a first ventilation passage for guiding gas that has passed through the end portion of the stator to the second cooler, a second ventilation duct for guiding gas that has passed through the stator ventilation duct to the first cooler, a third ventilation passage for guiding the gas that has passed through the stator ventilation duct to the first cooler, and the second ventilation passage for guiding the gas cooled in the second cooler to the rotor ventilation duct.

5. The electric rotating machine as defined in claim 1, wherein the rotor and the stator are encased in a housing, and the second cooler is disposed outside of the housing.

6. The electric rotating machine as defined in claim 1, wherein the rotor has windings wound on an iron core, and a retaining ring for holding the end portion of the windings, the fan being disposed adjacently to the outside of the retaining ring.

7. The electric rotating machine as defined in claim 1, wherein a ventilation improvement means is disposed in the vicinity of the entrance port of the first ventilation passage.

8. The electric rotating machine as defined in claim 7, wherein the ventilation improvement is to give a swirl motion to the gas.

9. The electric rotating machine as defined in claim 1, wherein the rotor and the stator are encased in a housing, and the first and second cooler are disposed in the housing.

10. The electric rotating machine as defined in claim 2, wherein the rotor and the stator are encased in a housing, and the second cooler is disposed outside of the housing.

11. The electric rotating machine as defined in claim 2, wherein the rotor has windings wound on an iron core, and a retaining ring for holding the end portion of the windings, the fan being disposed adjacently to the outside of the retaining ring.

12. The electric rotating machine as defined in claim 2, wherein a ventilation improvement means is disposed in the vicinity of the entrance port of the first ventilation passage.

13. The electric rotating machine as defined in claim 12, wherein the ventilation improvement is to give a swirl motion to the gas.

14. The electric rotating machine as defined in claim 2, wherein the rotor and the stator are encased in a housing, and the first and second cooler are disposed in the housing.

15. The electric rotating machine as defined in claim 3, wherein the rotor and the stator are encased in a housing, and the second cooler is disposed outside of the housing.

16. The electric rotating machine as defined in claim 3, wherein the rotor has windings wound on an iron core, and a retaining ring for holding the end portion of the windings, the fan being disposed adjacently to the outside of the retaining ring.

17. The electric rotating machine as defined in claim 3, wherein a ventilation improvement means is disposed in the vicinity of the entrance port of the first ventilation passage.

18. The electric rotating machine as defined in claim 17, wherein the ventilation improvement is to give a swirl motion to the gas.

19. The electric rotating machine as defined in claim 3, wherein the rotor and the stator are encased in a housing, and the first and second cooler are disposed in the housing.

20. The electric rotating machine as defined in claim 1, wherein the rotor and the stator are encased in a housing, and the second cooler is disposed outside of the housing.

21. The electric rotating machine as defined in claim 4, wherein the rotor has windings wound on an iron core, and a retaining ring for holding the end portion of the windings, the fan being disposed adjacently to the outside of the retaining ring.

22. The electric rotating machine as defined in claim 4, wherein a ventilation improvement means is disposed in the vicinity of the entrance port of the first ventilation passage.

23. The electric rotating machine as defined in claim 22, wherein the ventilation improvement is to give a swirl motion to the gas.

24. The electric rotating machine as defined in claim 4, wherein the rotor and the stator are encased in a housing, and the first and second cooler are disposed in the housing.

* * * * *

UNITED STATES PATENT AND TRADEMARK OFFICE
CERTIFICATE OF CORRECTION

| | | |
|---|---|---|
| PATENT NO. | : 7,294,943 B2 | Page 1 of 1 |
| APPLICATION NO. | : 11/265227 | |
| DATED | : November 13, 2007 | |
| INVENTOR(S) | : Kenichi Hattori et al. | |

It is certified that error appears in the above-identified patent and that said Letters Patent is hereby corrected as shown below:

On the title page of the Letters Patent, page 2,

Under section (56) References Cited, Foreign Patent Documents, add:
-- JP 5816042A  07-1983  Koyahata --

Signed and Sealed this

Twenty-third Day of September, 2008

JON W. DUDAS
*Director of the United States Patent and Trademark Office*